United States Patent
Harton

(10) Patent No.: US 9,578,859 B2
(45) Date of Patent: Feb. 28, 2017

(54) TRANSGENIC MICE EXPRESSING HUMAN PYRIN DOMAIN ONLY PROTEIN 2

(71) Applicant: Albany Medical College, Albany, NY (US)

(72) Inventor: Jonathan A. Harton, Slingerland, NY (US)

(73) Assignee: ALBANY MEDICAL COLLEGE, Albany, NY (US)

( * ) Notice: Subject to any disclaimer, the term of this patent is extended or adjusted under 35 U.S.C. 154(b) by 0 days.

(21) Appl. No.: 14/989,134

(22) Filed: Jan. 6, 2016

(65) Prior Publication Data

US 2016/0192627 A1    Jul. 7, 2016

Related U.S. Application Data

(60) Provisional application No. 62/100,104, filed on Jan. 6, 2015.

(51) Int. Cl.
  *C12N 15/85* (2006.01)
  *A01K 67/027* (2006.01)

(52) U.S. Cl.
  CPC ...... *A01K 67/0278* (2013.01); *C12N 15/8509* (2013.01); *A01K 2207/15* (2013.01); *A01K 2227/105* (2013.01); *A01K 2267/0368* (2013.01); *C12N 2015/8527* (2013.01)

(58) Field of Classification Search
  CPC ............ A01K 67/0278; A01K 2207/15; A01K 2227/105; A01K 2267/0368; C12N 15/8509; C12N 2015/8527
  See application file for complete search history.

(56) References Cited

PUBLICATIONS

Gao et al., Scientific Reports, 5: 16284, pp. 1-12, 2015.*
Rocha-Martins, An. Acad. Bras. Cienc., 87(2 Suppl.), 1323-1348, 2015.*
Ryan et al., Sem. Neph. 22:154-160, 2002.*
Holschneider et al., Int J. Devl. Neuroscience 18:615-618, 2000.*
Barthold, Genetica, 122: 75-88, 2004.*
Liu et al., Methods Mol. Biol., 1027: pp. 1-15, 2013.*
Atianand et al., BMC Evolutionary Biology, 11(56), pp. 1-10, 2011.*

* cited by examiner

*Primary Examiner* — Thaian N Ton
(74) *Attorney, Agent, or Firm* — David L. Nocilly; Bond, Schoeneck & King, PLLC

(57) ABSTRACT

A transgenic mouse expressing the human gene for PYRIN domain-only protein 2 (POP2). POP2, when expressed in the transgenic mouse model, broadly dampens inflammatory cytokine production, in part through restricting the activation of both Nlrp3 and Aim2 inflammasomes. POP2 mice exhibit reduced susceptibility to LPS- and bacteria-induced septic shock. Further, POP2 mice are less susceptible to the fatal, acute inflammatory pneumonia caused by pulmonary infection with *F. tularensis* LVS and *F. novicida*, which are highly pathogenic to mice, but non-pathogenic to humans.

8 Claims, 12 Drawing Sheets

TRANSGENIC MICE EXPRESSING HUMAN PYRIN DOMAIN ONLY PROTEIN 2

CROSS-REFERENCE TO RELATED APPLICATIONS

Figure 1:
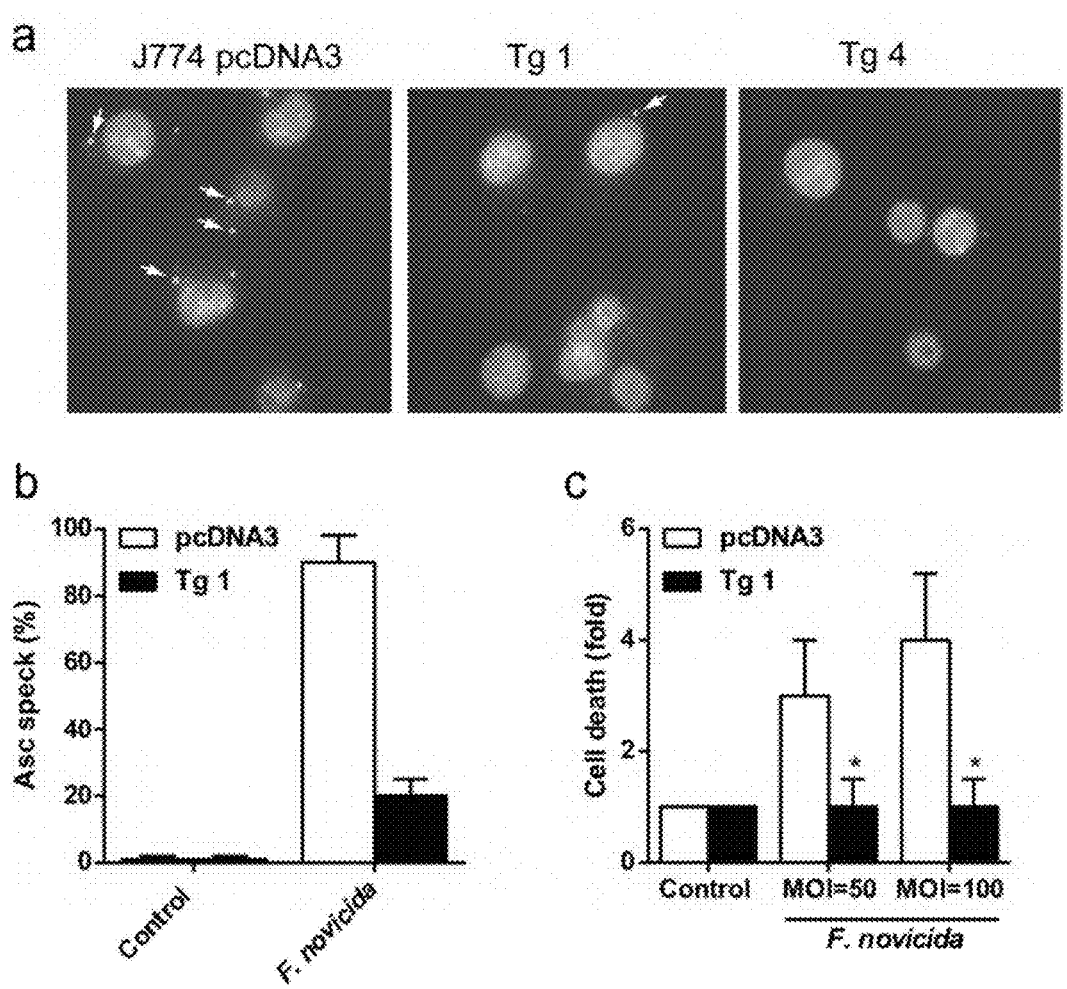

The present application claims priority to U.S. Provisional Application No. 62/100,104, filed on Jan. 6, 2015.

STATEMENT REGARDING FEDERALLY SPONSORED RESEARCH

This invention was made with government support under Grant No. R01 AI072259 awarded by the National Institute of Allergy and Infectious Diseases (NIAID) of the National Institutes of Health (NIH). The government has certain rights in the invention.

BACKGROUND OF THE INVENTION

1. Field of the Invention

The present invention relates to transgenic mouse models and, more particularly, to a transgenic mouse expressing human Pyrin-domain only (PYD) protein 2 (POP2).

2. Description of the Related Art

Inflammation is critical for clearing infections and responding to injury. However, excessive or prolonged inflammation contributes to irreversible tissue damage and the dysfunction of vital organs. Pro-inflammatory chemokines and cytokines, such as TNFα, IL-6, IL-8 and IL-1β, mediate inflammation. Most of these mediators are readily secreted as active form upon signal-induced synthesis, while the release of some other cytokines is tightly controlled. For example, the production of leaderless cytokines, such as IL-1 and IL-18, is controlled by several layers of enzymatic processes; (i) IL-1 or IL-18 is synthesized as a pro-form, which is cleaved by caspase-1 (a cysteine protease), (ii) the caspase-1, itself, is also synthesized as a pro-caspase-1, which is cleaved into active caspase-1 by inflammasome, and (iii) the inflammasome is a multi-protein complex structure formed by two or more proteins scattered in the cytoplasm, wherein they form a platform for self-cleaving of pro-caspase-1 into active caspase-1. Thus, the involvement of many steps in processing these cytokines highlights the importance of possible regulatory molecules that control unfettered activation and release of these cytokines as to avoid harmful effects in mammalian host.

Although the assembly of inflammasome structure is initiated by cytosolic sensors belonging to either the nod-like receptor (NLR) or the PYHIN family. NLR family proteins (e.g. NLRP3 and NLRC4) require an evolutionarily conserved Pyrin (PYD) or caspase recruitment domain (CARD), while members of the PYHIN family (e.g. AIM2) rely solely on a PYD. A homotypic PYD-PYD interaction between the sensor and apoptotic speck-like protein containing a CARD (ASC) is followed by recruitment of pro-caspase-1 via a CARD-CARD interaction.

Recently, viral and mammalian PYRIN domain-only proteins (POPs), comprised of essentially a solitary PYD, have been identified as likely regulators of inflammatory processes by inhibiting the NF-kB p65 signaling, limiting inflammasome formation, or both. Among mammalian species, POPs are evolutionarily recent, highly conserved, and appear to be restricted to higher primates, implying a unique role for these proteins in modulating the inflammatory responses. The recent identification and characterization of POP3 and an initial description of POP4 brings the number of human POP family members to four; all of which lack homologs in mice.

POP1 is expressed in human monocytes, macrophages and granulocytes, while POP2 in human testis, lymphocytes and macrophages. Moreover, knockdown of POP2 in human cells or stable expression in mouse cells has revealed the capacity of POP2 to limit the production of both TNFα and IL-1β. A recent study reported that POP3 is expressed in human monocyte and macrophages, but not B cells and T cells. POP4 exhibits a broad constitutive expression, but is induced in human macrophages. Functionally, POP1 inhibits IKKα and β, but it does not inhibit the NLRP3 inflammasome. However, POP2 impairs both NF-κB activation and NLRP3 inflammasomes; thereby limiting the production of both TNFα and IL-1β. Inhibition of NF-κB signaling by POP2 occurs at the level of NF-κB p65, likely through altering nuclear translocation of p65 and reducing the transactivation capacity of the RelA/p65 NF-κB transactivation domain 1. POP2 also reduces formation of NLRP3 inflammasomes by disrupting PYD-PYD interaction between ASC and NLRP3. The minimum peptide and specific residues of POP2 required for restricting both NF-kB activity and the NLRP3 inflammasome have been elucidated in in vitro cultured cells. Interestingly, POP3 has been shown to specifically inhibit the AIM2 inflammasome, but not that of NLRP3, while POP4 maintains a POP2-like NF-kB inhibitory capacity, but is likely not an inflammasome inhibitor.

Since mice lack the POP2 gene (as do all non-primate species), no knockout mouse model exists to elucidate the in vivo function of POP2. Thus, the exploration of POP2 function to date has been restricted to in vitro cellular models. Moreover, the creation of a mouse model using conventional approaches that results in overexpression of the relevant gene or a tissue expression pattern that is random will not be effective for replicating the expression of the gene in humans. Consequently, there is a need in the art for a mouse model that expresses POP2 in a manner consistent with the way the protein is expressed in humans and thus can be used to understand and evaluate the physiologic role of POP2 in humans.

BRIEF SUMMARY OF THE INVENTION

The present invention comprises humanized mice expressing PYDC2 (POP2) represent an animal model for the regulation of inflammatory signaling by the primate-restricted POP2 protein. As POP2 is absent in small animal models used for human disease research, POP2 humanized mice represent a powerful tool for investigation of the function of POP2 in human health and disease, the impact of human drug treatments for inflammation-related conditions on the key regulatory pathways influenced by POP2, and a vehicle for testing therapeutics designed to enhance or restrict the action of POP2 to influence immunity. POP2 regulates late p65-mediated events in the NF-kB signaling pathway involved in inflammation, cell proliferation, cell survival, cellular differentiation, and cellular activation. POP2 also regulates the activation of the NLRP3 and AIM2 inflammasomes linked to a variety of human diseases including influenza, rheumatoid arthritis, Type II diabetes, gout, atherosclerotic heart and vascular disease, and septic shock. Further, the normal immune response to vaccines and infections also involve activation of the NLRP3 and/or AIM2 inflammasome as well as the NF-kB pathway. As POP2 regulates both of these inflammasomes together with the activation of NF-kB, humanized POP2 mice are a valuable resource for probing these connections.

The mice were been produced on the C57BL/6 genetic background (backcrossed for >9 generations) and extensively characterized for expression of POP2 in hematopoietic cells and tissues. Testing of the mice demonstrated that inflammatory processes controlled by POP2 are regulated in the mice (reduced cytokine production upon exposure to endotoxin and infection, including TNFalpha, IL-6, IL-1beta, IL-12, and others). Additionally, testing revealed data demonstrating that POP2 alters the outcome of inflammatory and infectious challenges to these mice.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 1 is a series of graphs showing that POP2 blocks the Nlrp3 and Aim2 inflammasomes and bacteria-induced cell death in murine macrophages, where: (a) J774A.1 cells expressing pcDNA3 or POP2 Tg were infected with $F.$ $novicida$ (MOI=100) and Asc-speck formation (indicated by arrows) was identified by microscopy; (b) Asc-specks were quantified as percent specks formed; and (c) J774A.1 cells expressing pcDNA3 or POP2 Tg were infected with $F.$ $novicida$ (MOI=50 or 100) and the frequencies of dead cells (PO was measured by flow cytometry at 24 h.

Figure 2:
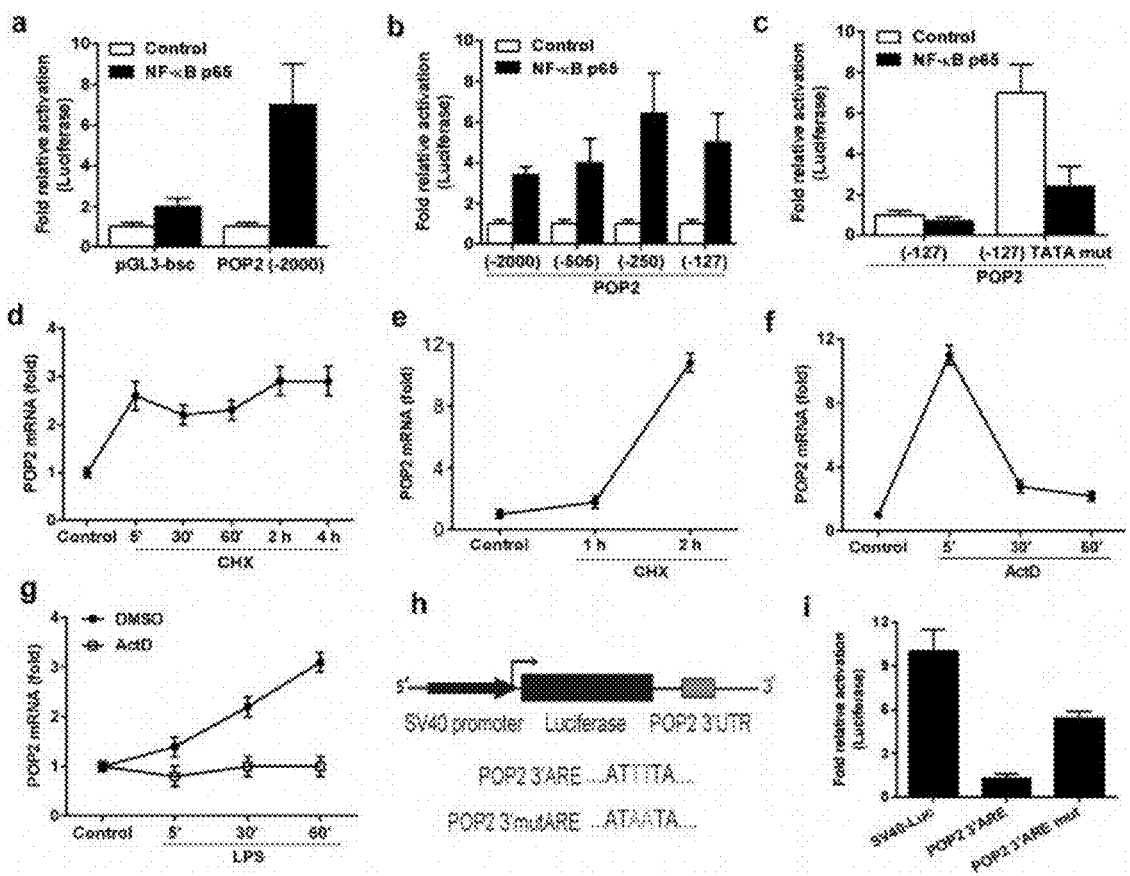

FIG. 2 is a series of graphs characterizing the POP2 transcriptional and post-transcriptional regulatory elements, where: (a) Luciferase assays with constructs containing the −2000 region upstream of the POP2 ATG with and without NF-κB p65 subunit in HEK-293T cells; (b) Luciferase assays using 5' truncations of the −2000 POP2 promoter with NF-κB p65 in HEK-293T cells; (c) Luciferase assays using constructs with WT and TATA-box mutations in the −127 POP2 promoter region in HEK-293T cells; (d) POP2 mRNA expression in THP-1 cells treated with cycloheximide (CHX); (e) POP2 expression in U937 cells treated with CHX; (f) POP2 mRNA half-life was determined by inhibition of transcription with ActD following LPS stimulation; (g) Confirmation of inhibition of POP2 mRNA transcription by ActD; (h) A model for WT POP2 3'UTR or 3'ARE mutant constructs; and (i) Luciferase assays in HeLa cells transfected with either WT POP2 3'UTR or 3'ARE mutant constructs.

Figure 3:
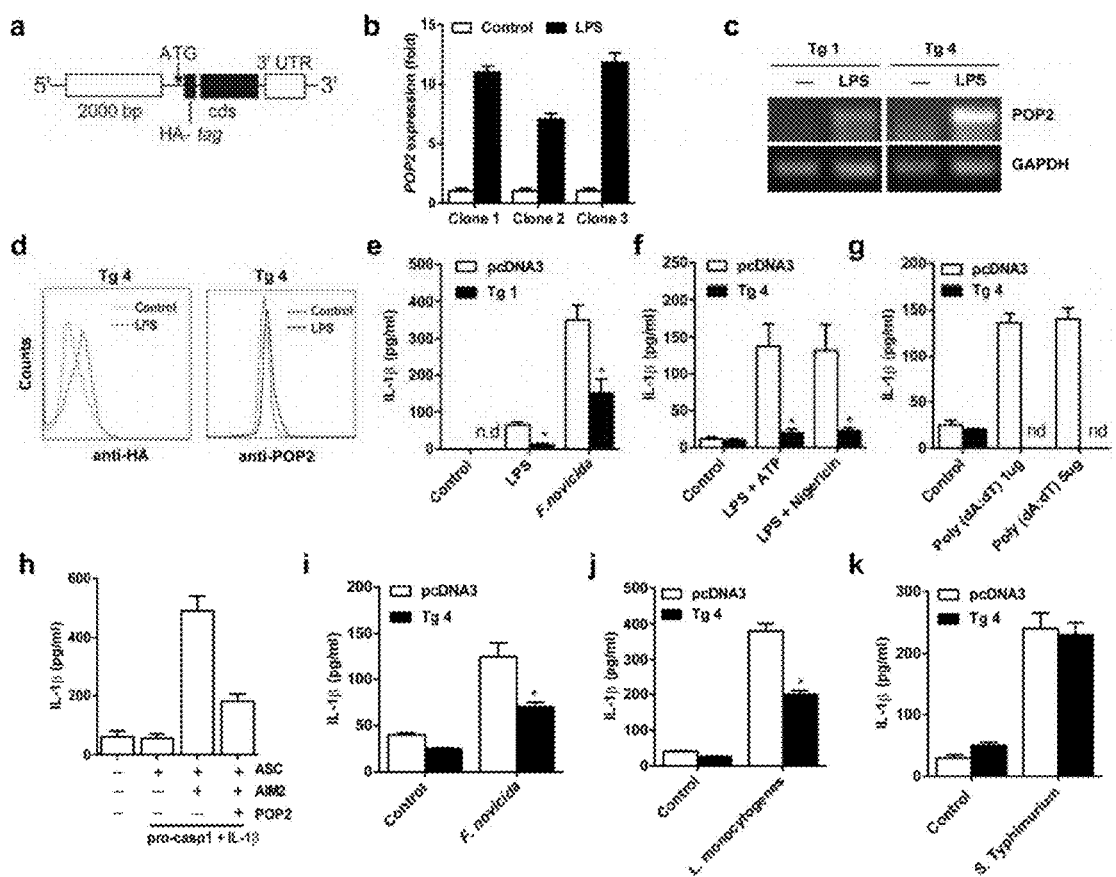

FIG. 3 is a series of graphs of the genetic reconstitution of human POP2 into murine macrophages recapitulates its function: where (a) A model of POP2 Tg construct containing −2000 bp of the POP2 promoter, HA-tag and the complete 3'UTR to the poly-A tail for genetic reconstitution into murine macrophages; (b) POP2 Tg construct transfected in RAW264.7 cells prevented constitutive expression but induced POP2 mRNA following LPS (100 ng/ml) stimulation; (c) Detection of POP2 mRNA expression in stable transfected J774A.1 cells by RT-PCR after LPS (100 ng/ml) stimulation; (d) Detection of POP2 protein expression in stably transfected J774A.1 cells by flow cytometry using anti-HA tag or anti-POP2 antibodies after LPS (100 ng/ml) stimulation; (e) IL-1β mRNA expression measured by qPCR in pcDNA3 or POP2 Tg J774A.1 cells following LPS (100 ng/ml) or $F.$ $novicida$ (MOI=100) treatment for for 24 h; (f) Level of mature IL-1β measured by ELISA in culture supernatents of LPS-primed pcDNA3 or POP2 Tg J774A.1 cells following ATP (5 mM) or nigericin (10 μM) treatment for 30 min; (g) Level of mature IL-1β measured by ELISA in culture supernatents of pcDNA3 or POP2Tg J774A.1 cells transfected with poly (dA:dT) (1 μg/ml) for 18 h; (h) Level of mature IL-1β measured by ELISA in HEK293T ells were transiently transfected with ASC, AIM2 and/or POP2 constructs for 20 h; (i). Mature IL-1β in pcDNA3 or POP2 Tg J774A.1 cells infected with $F.$ $novicida$ (MOI=100) for 24 h; (j) Mature IL-1β in pcDNA3 or POP2 Tg J774A.1 cells infected with $L.$ $monocytogenes$ (MOI=5) for 6 h; and (k) Mature IL-1β in pcDNA3 or POP2 Tg J774A.1 cells infected with $S.$ $Typhimurium$ (MOI=10) for 6 h. *P<0.05 (Student's t-test (b-k)).

Figure 4:
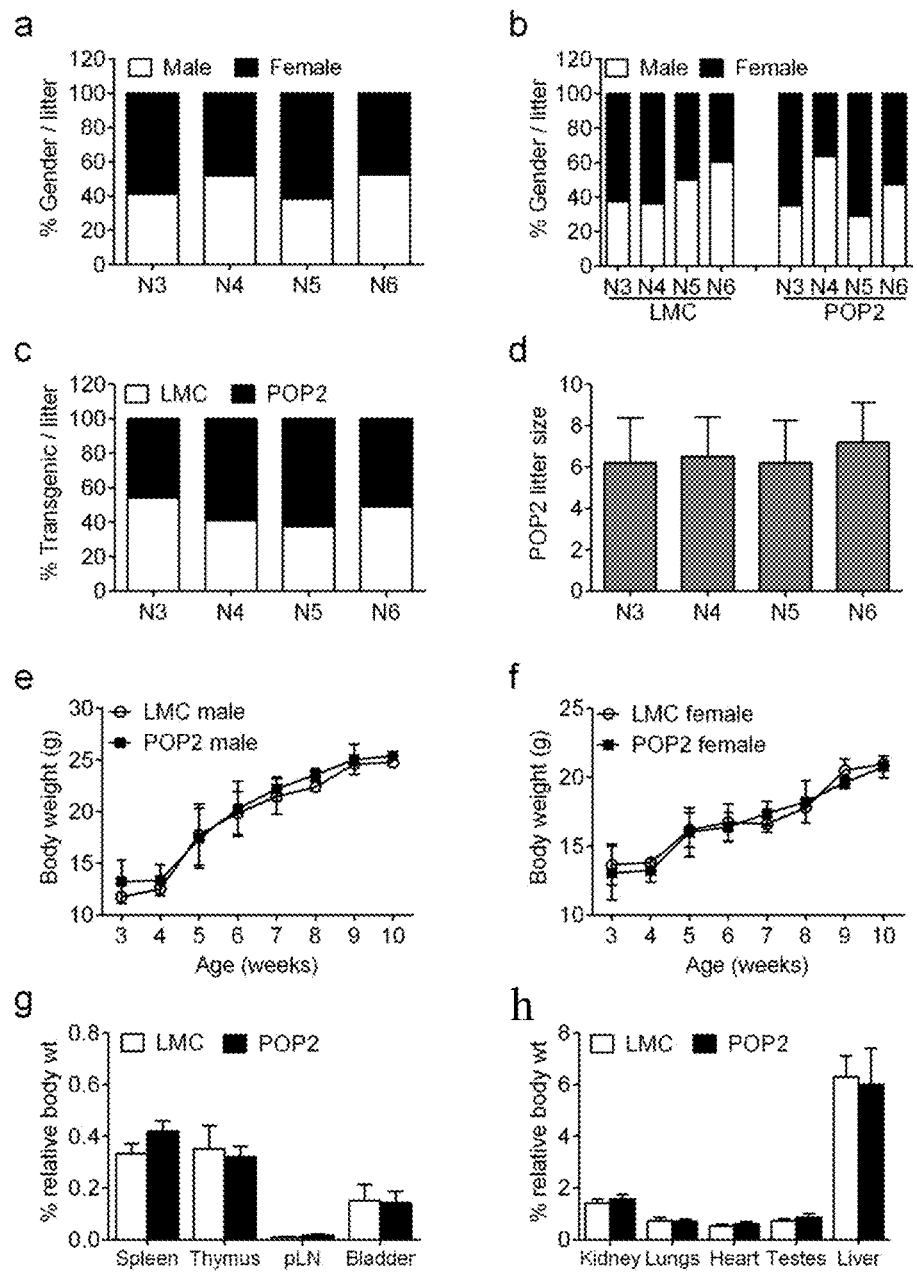

FIG. 4 is a series of graphs showing the general phenotyping of POP2Tg mice. (a) Percent gender per litter as a whole. (b) Percent gender per litter among POP2Tg and LMC mice separately. (c) Percent POP2Tg mice per litter. (d) The frequency of Pop2 litter size. (e) Body weight of male POP2Tg and LMC mice (f) Body weight of female POP2Tg and LMC mice. (g-h) Percent organ weights relative to body weights.

Figure 5:
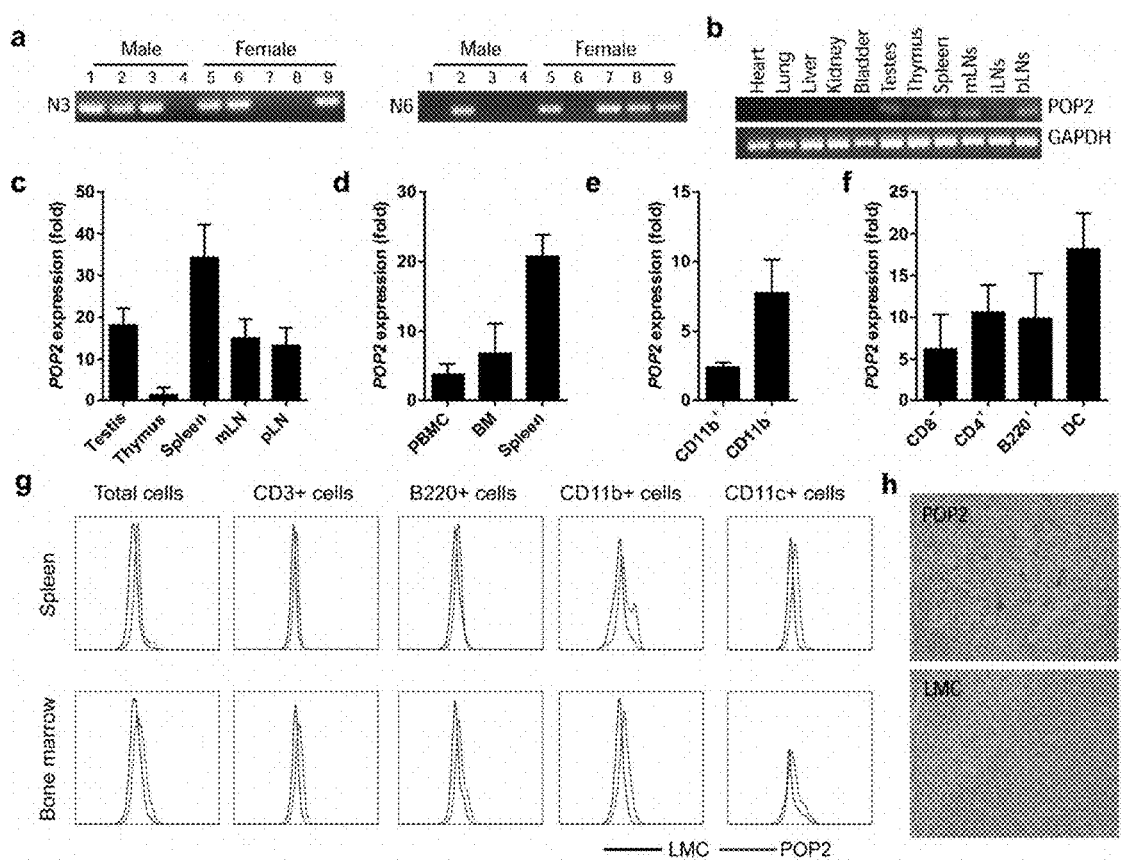

FIG. 5 is a series of graphs of the generation of human POP2 Tg mouse. POP2 Tg mice were generated by pronuclear microinjection of POP2 Tg construct shown in FIG. 2$a$ into fertilized oocytes/eggs of DBA/2 mice, where: (a) Genotyping of POP2 transgenic mice (N3 and N6 generations) by in-house standardized PCR using genomic DNA obtained from ear-punch; (b) Detection of POP2 Tg expression by RT-PCR in various tissues; (c) Quantitation of POP2 Tg expression in different tissues by qPCR; (d) Quantitation of POP2 Tg expression in PBMC, bone marrow cells and splenocytes by qPCR; (e) Quantitation of POP2 Tg expression in CD11b$^+$ and CD11b$^-$ fractions of bone marrow cells; (f) Quantitation of POP2 Tg expression in different subsets of splenocytes by qPCR; (g) Confirmation of POP2 protein expression by intracellular staining with anti-POP2 antibody in subsets of splenocytes and bone marrow cells by flow cytometry; (h) Detection of POP2 expression in formalin-fixed tissue section of spleen by immunohistochemical staining with anti-POP2 antibody and hematoxylin counter-staining. A representative data is presented from at least two independent experiments (a,b, g,h).

Figure 6:
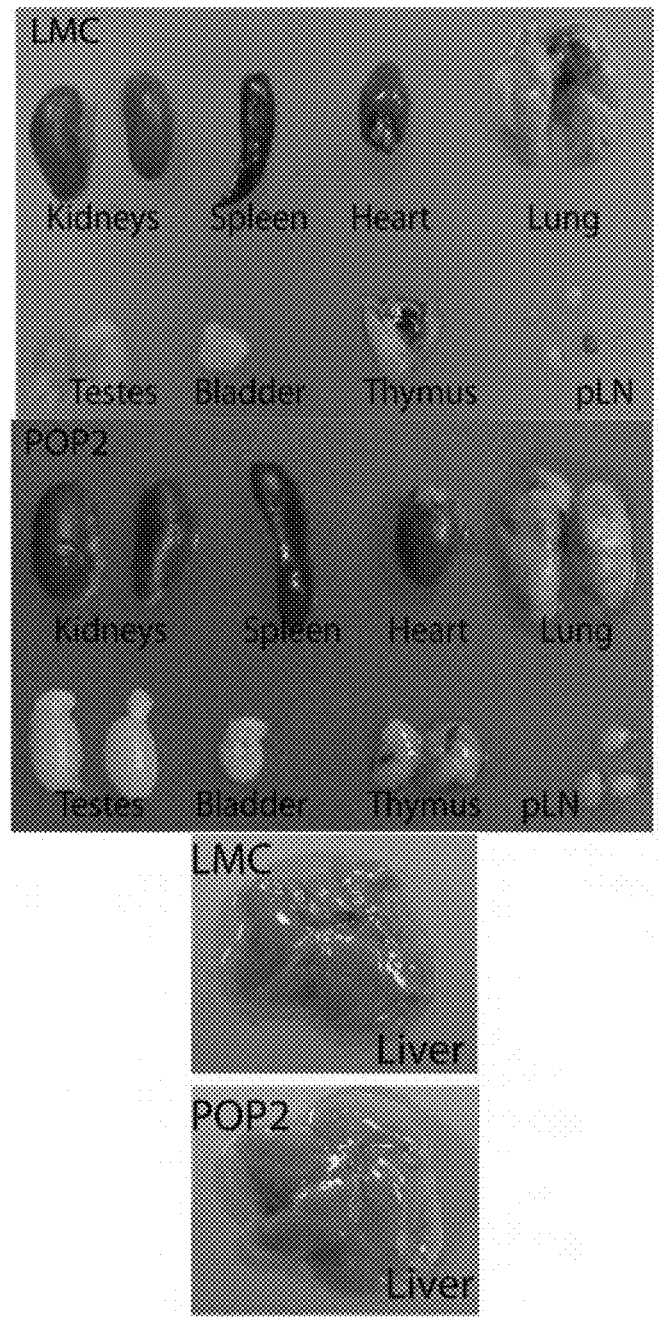

FIG. 6 is a series of images showing the gross evaluation of tissues of POP2Tg and LMC mice. Gross anatomy of different tissues showing normal structures from POP2Tg and LMC mice. Gross images are representative of two independent experiments.

Figure 7:
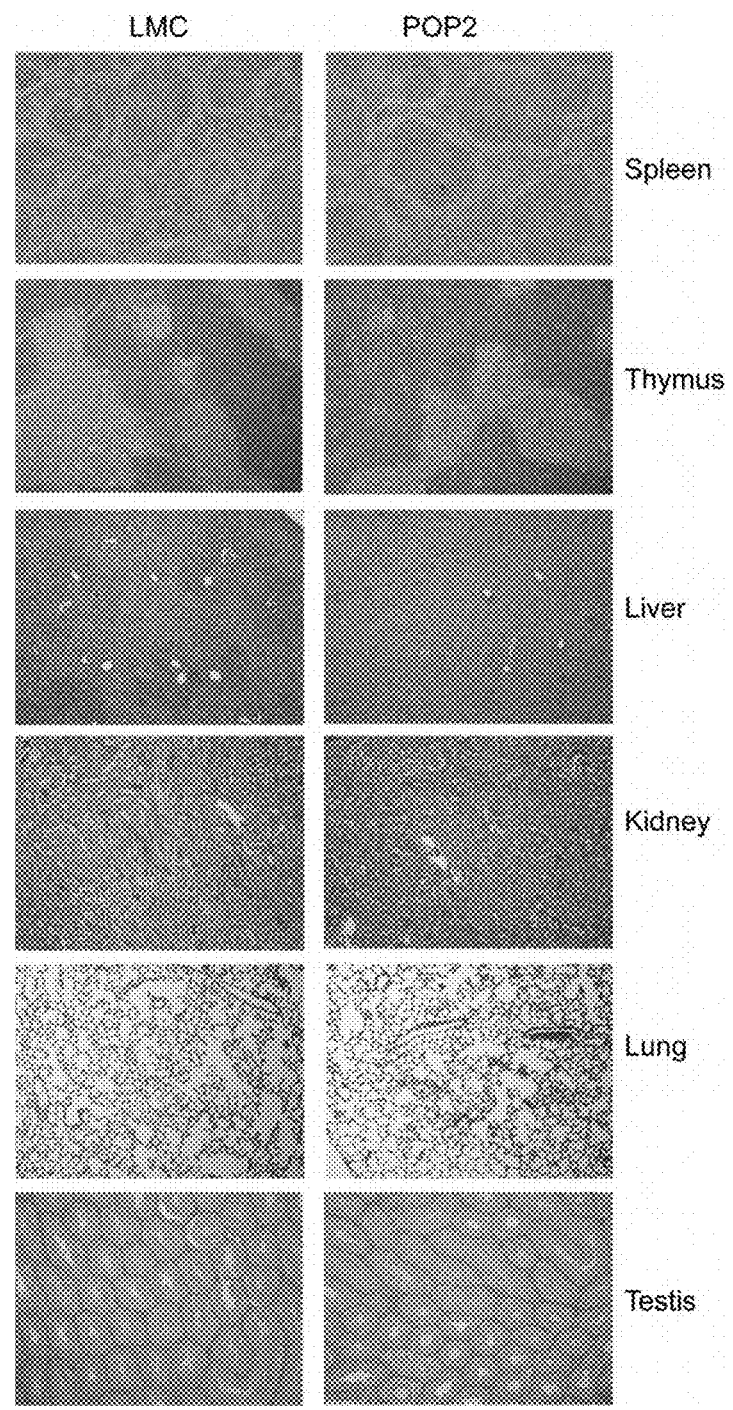

FIG. 7 is a series of images of the histological evaluation of tissues of POP2Tg and LMC mice. Microscopic anatomy of tissue sections showing normal structures of spleen, thymus, liver, kidney, lung and testes from LMC and POP2Tg mice. Tissue sections were stained with hematoxylin and eosin and analysed in light microscopy. Microscopic images are representative of two independent experiments.

Figure 8:
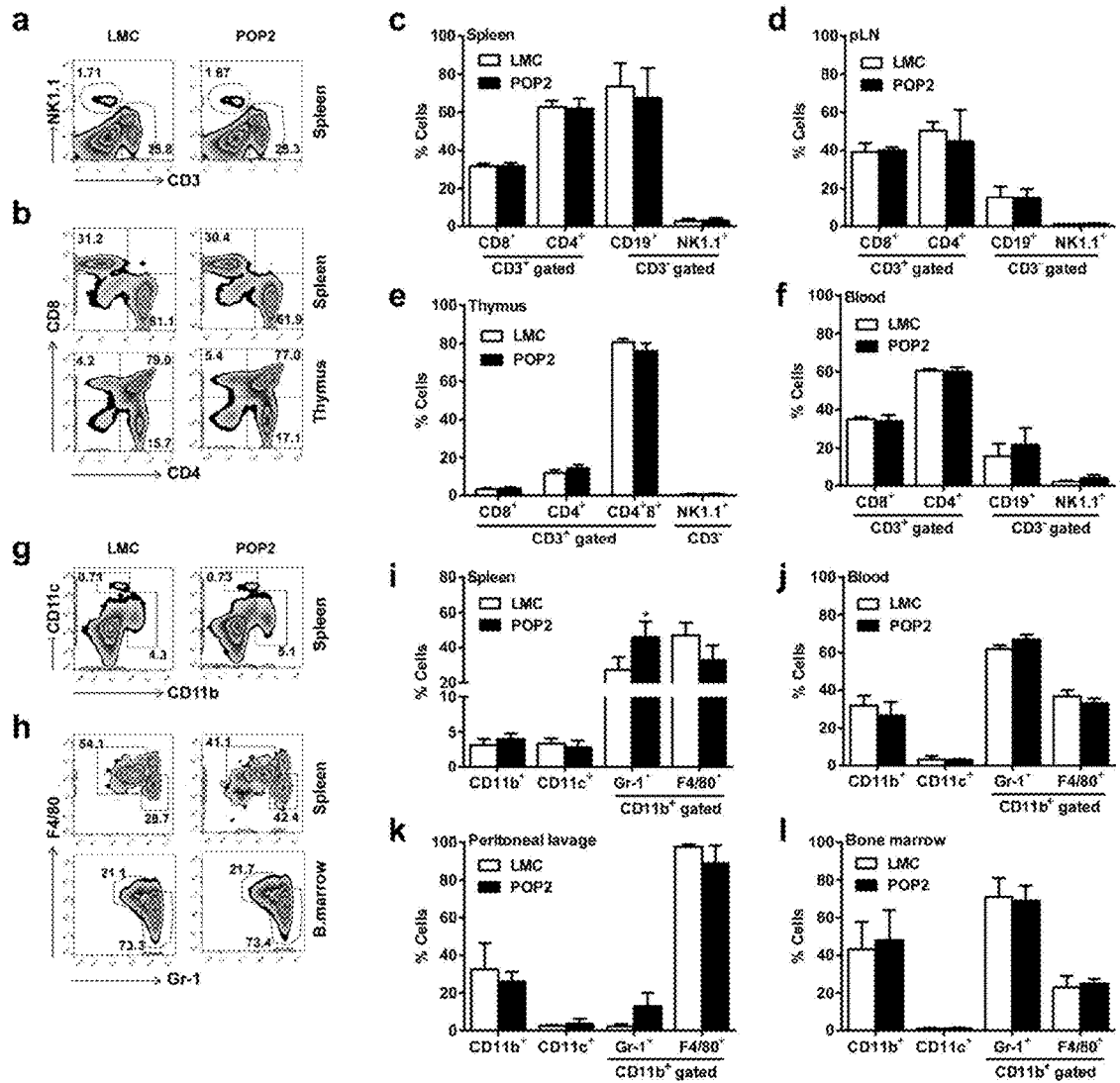

FIG. 8 is a series of graphs of immunophenotyping of POP2 Tg mice, where (a-b) Representative histograms for multi-color flow cytometry analyses of lymphoid cells in POP2 and litter mate control (LMC) mice; (c-f) The frequencies of lymphoid cells in spleen, pLN, thymus and peripheral blood; (g-h) Representative histograms for flow cytometry analyses of myeloid-lineage cells in POP2 and LMC mice. The major myeloid lineage cell populations were identified as neutrophils (CD11b$^+$CD11c$^-$Gr-1$^+$F4/80$^-$), macrophages (CD11b$^+$CD11c$^-$Gr-1$^-$ F4/80$^+$) and DC (CD11c$^+$CD11b$^{low/-}$Gr-1$^-$F4/80$^-$); and (i-l) The frequencies of myeloid cells in spleen, peripheral blood, peritoneal fluid and bone marrow. *P<0.05, (Student's t-test (i)). Data are from at least two independent experiments (mean and s.d) (c-l)

Figure 9:
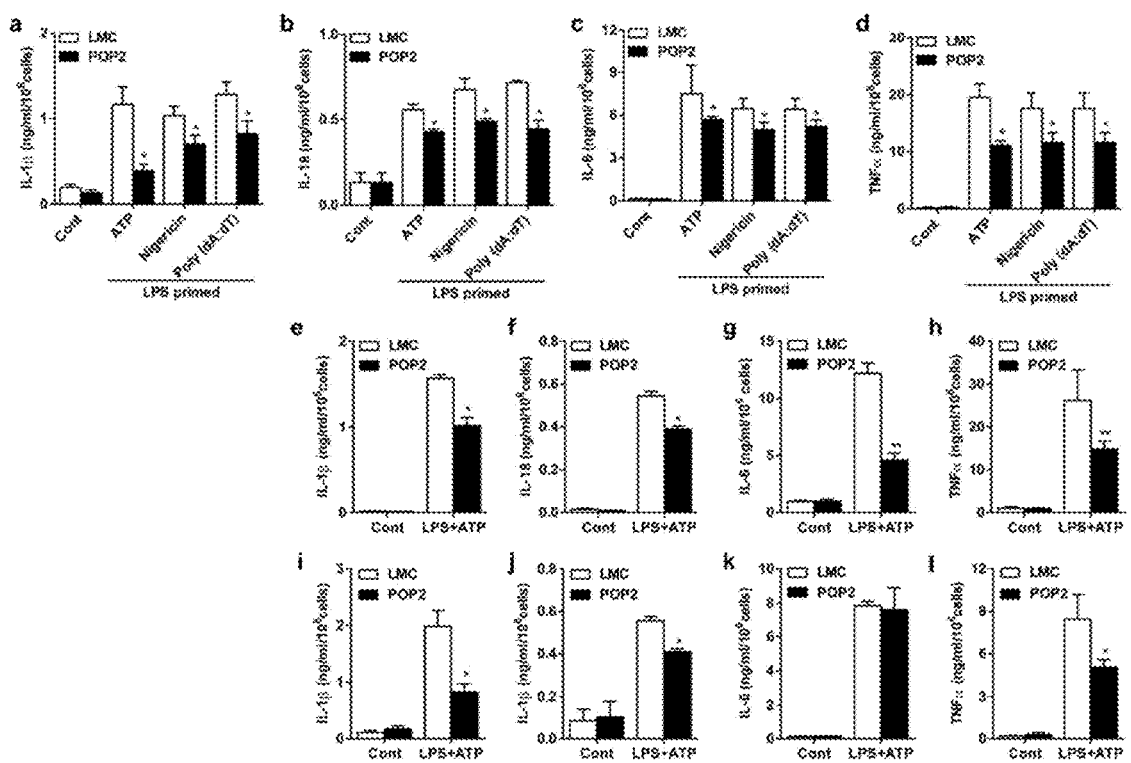

FIG. 9 is a series of graphs of POP2 inhibition of the Nlrp3 and Aim2 inflammasomes-mediated release of cytokines in macrophages, where: (a-d) Level of cytokines produced by BMDM isolated from POP2Tg (n=4) and LMC (n=4) mice 24 h after stimulation with LPS (100 ng/ml) plus ATP (5 mM) or nigericin (10 µM) (for activation of Nlrp3 inflammasome), or transfected with poly (dA:dT) (for activation of Aim2 inflammasome). The cytokines were measured by luminex assay; (e-h) Level of cytokines produced by peritoneal macrophages isolated from POP2Tg (n=4) and LMC (n=4) mice 24 h after stimulation with LPS (100 ng/ml) plus ATP (5 mM). Resident peritoneal macrophages isolated by lavaging the peritoneal cavity with sterile PBS were cultured in DMEM and the adherent macrophages were stimulated with LPS. The cytokines were measured by luminex assay. (i-l) Level of cytokines produced by splenic macrophage isolated from POP2Tg (n=4) and LMC (n=4) mice 24 h after stimulation with LPS (100 ng/ml) plus ATP (5 mM). Splenic macrophages isolated by magnetic bead separation were cultured in DMEM and the adherent macrophages were stimulated with LPS. The cytokines were measured by luminex assay. *P<0.05, **P<0.01 (Student's t-test (a-l)).

Figure 10:
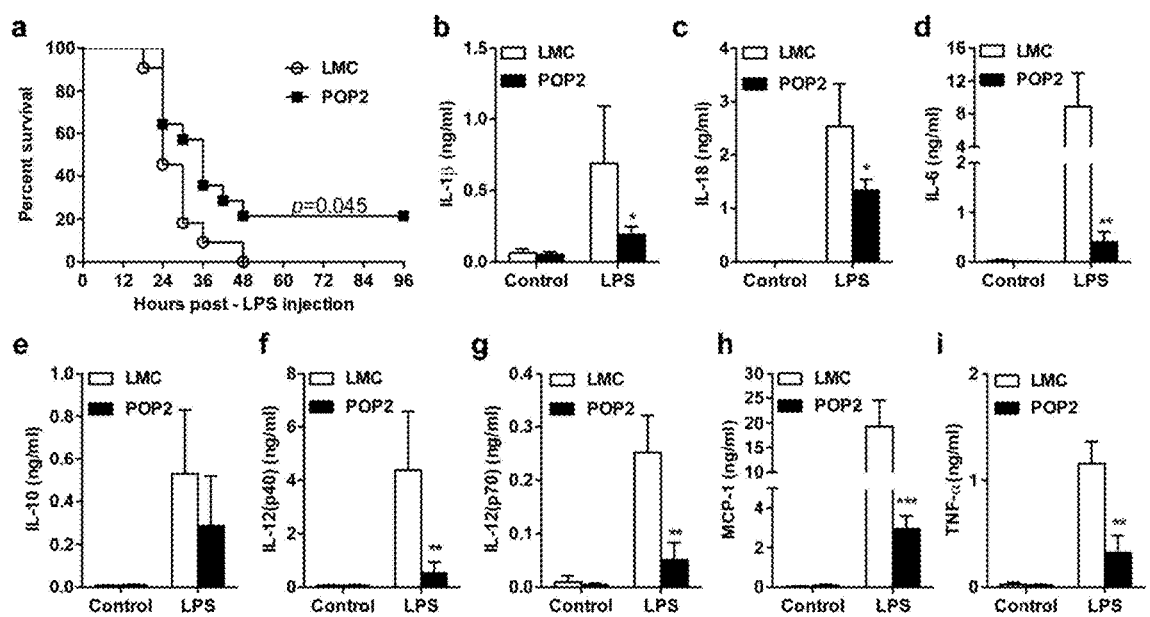

FIG. 10 is a series of graphs showing that POP2Tg mice exhibit resistance to LPS-induced shock, where (a) Survival of POP2 Tg (n=14) and LMC (n=12) mice following intraperitoneal injection with a lethal dose (50 mg/kg) of LPS (O55:B5); and (b-i) Serum levels of cytokines (IL-1β, IL-18, IL-6, IL-12, MCP-1, TNF-α and IL-10) measured by luminex assay in POP2 and LMC mice 24 h after injection with sublethal dose (15 mg/kg) LPS. *P<0.05, P<0.01, *P<0.001 (Log-rank test for survival (a) or Student's t-test (b-i)).

Figure 11:
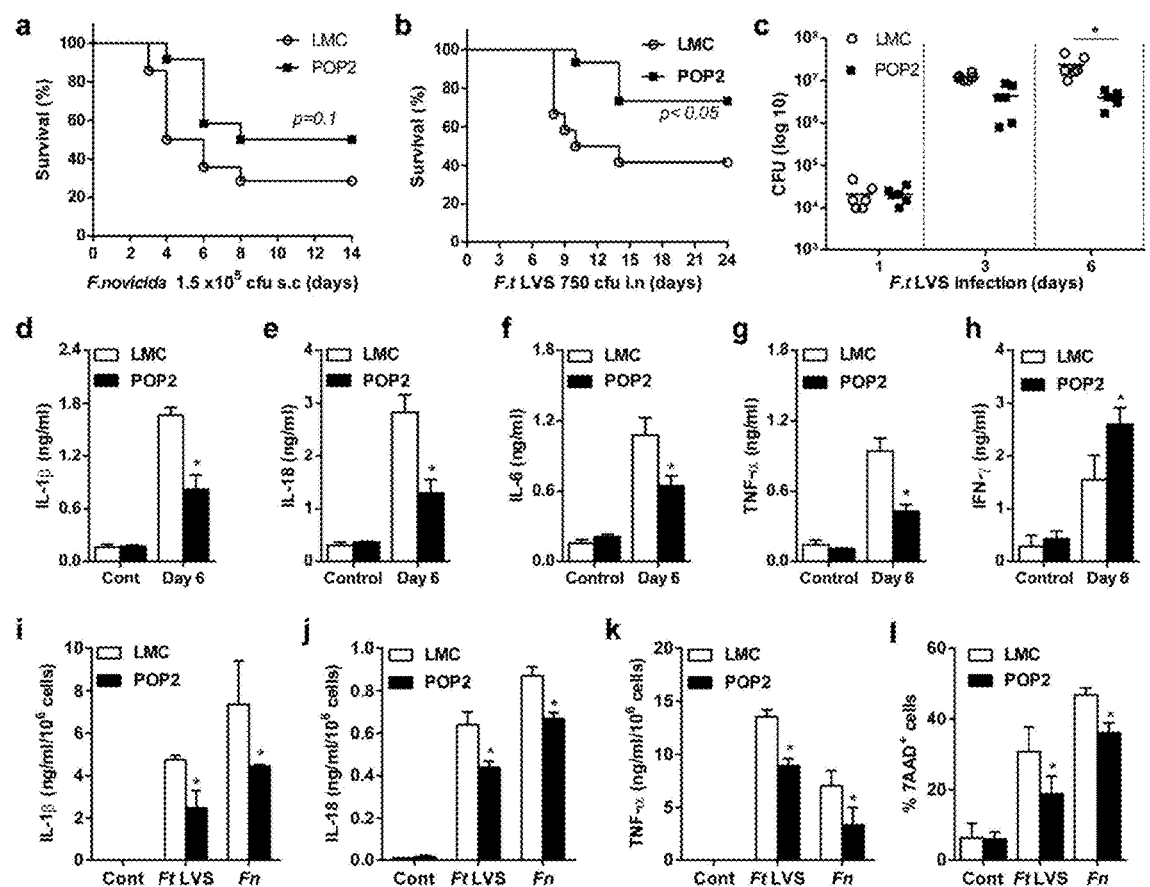

FIG. 11 is a series of graphs showing that POP2Tg mice are less susceptible to acute inflammation caused by bacterial infections, where: (a) Survival of POP2 Tg (n=12) and LMC (n=14) mice following s.c. infection with $1.5 \times 10^5$ cfu of F. novicida; (b) Survival of POP2 Tg (n=12) and LMC (n=14) mice following i.n. infection with 750 cfu of F. tularensis LVS; (c) Bacterial burden in lungs of POP2Tg and LMC mice infected i.n. with 1000 cfu of F. tularensis LVS at 1, 3 and 6 days post-infection; (d-h) The levels of cytokines (mature IL-1β and IL-18, IL-6, TNF-α and IFN-γ) measured by luminex assay in the lung homogenates of POP2Tg and LMC mice infected i.n. with 1000 cfu of F. tularensis LVS; (i-k) The levels of mature IL-1β and IL-18, and TNF-α measured by luminex assay in 24 h culture supernatents of BMDM infected with F. tularensis LVS (F.t) or F. novicida (F.n) at MOI=100; and (l) The frequency of dead cells (7-AAD$^+$) analyzed by flow cytometry in BMDM infected with F. tularensis LVS (F.t) or F. novicida (F.n) at MOI=100 after 24 h. *P<0.05 (Wilcoxon test for survival (a), Log-rank test for survival (b) or Student's t-test (c-l)).

Figure 12:
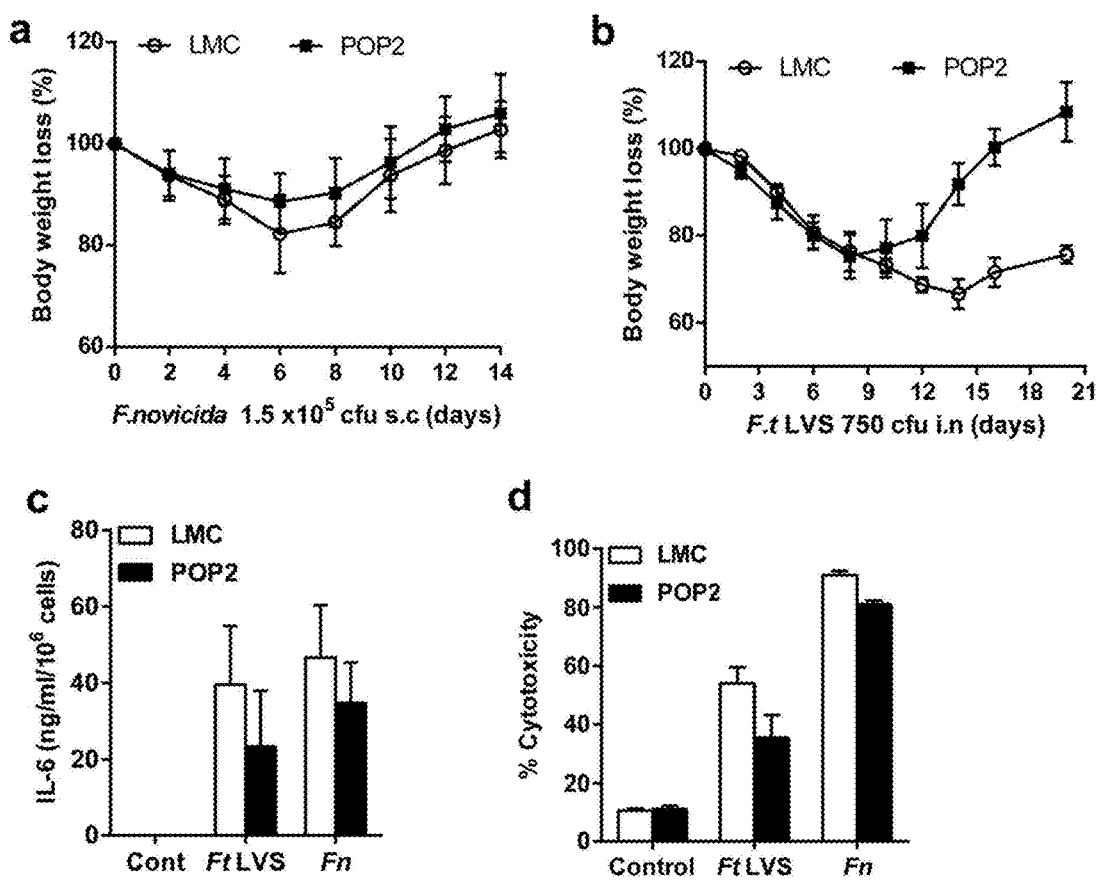

FIG. 12 is a series of graphs showing that POP2Tg mice are less susceptible to acute inflammation caused by bacterial infections, where: (a) Loss of body weight in POP2 Tg (n=12) and LMC (n=14) mice following s.c. infection with $1.5 \times 10^5$ cfu of F. novicida; (b) Loss of body weight in POP2 Tg (n=12) and LMC (n=14) mice following i.n. infection with 750 cfu of F. tularensis LVS; (c) The levels of IL-6 measured by luminex assay in 24 h culture supernatents of BMDM infected with F. tularensis LVS (F.t) or F. novicida (F.n) at MOI=100; and (d) The percent cytotoxicity calculated by LDH release assay in BMDM infected with F. tularensis LVS (F.t) or F. novicida (F.n) at MOI=100 after 24 h. *P<0.05 (Student's t-test).

DETAILED DESCRIPTION OF THE INVENTION

Referring now to the drawings, wherein like reference numerals refer to like parts throughout, the present invention comprises the creation of a transgenic mouse model that would largely recapitulate the expression and function of human POP2. The model may be used to address the in vivo role of POP2 and to gain insight into its function in human health and disease. To better understand POP2 gene expression and achieve similar expression in a mouse, the "minimal" promoter elements required for POP2 transcription were identified. The POP2 promoter is likely contained within the 300 bp immediately upstream of the POP2 translation start site of the POP2 sequence (SEQ ID NO: 1). Such a short promoter is consistent with the observation that other newly emergent genes have short promoters. Nevertheless, 2000 bp upstream of the ATG (SEQ ID NO: 2) were used as an example of the present invention out of caution, and it should be recognized by those of skill in the art that there is always the possibility of distal enhancers or repressor sequences that are absent from the example of the invention yet involved in the regulation of POP2 expression.

For example, NLRP2, the "parent gene" of POP2, has a 5' distal start site 4000 bp from its start codon, but the 5' region of POP2 does not contain these NLRP2 sequences. Moreover, the emergence of POP2 is likely the result of a retrotransposition event, rather than one of classical gene duplication. While sequence analysis did not identify a transcription start site (TSS), suggesting POP2 may have a dispersed promoter recognized by RNA Pol II, a potential TFIIB binding site (TATA box) and two Inr elements that represent potential binding sites for TFIID were identified. The potential lack of a focused promoter is not surprising. Such promoters are more archaic, being found in early eukaryotes but less often in vertebrates, consistent with the late date (~25 million years ago) and the primate-specificity of POP2. In contrast, the POP2 promoter does contains a TATA box, commonly associated with more primordial species and focused promoters. Experimental data demonstrates that very little of the POP2 5'UTR (127 nt) is required for NF-κB mediated expression. Searches based on the IκBα promoter NF-κB p65 binding sites, revealed two putative NF-κB p65 binding sites in the POP2 5'UTR located at −24 (NF-κB 1) and −36 bp (NF-κB 2) upstream of the ATG start codon. Preliminary results suggest that both may be involved (data not shown). The TATA box is important and likely required for NF-κB/p65-mediated POP2 transcription as the transcription activation domain 1 (TAD1) of NF-kB/p65 is known to associate with the TATA-box binding proteins TFIIB and TBP. Further, glucocorticoids silence NF-κB transcription of proinflammatory genes by disrupting p65 association with basal transcription machinery at the TATA box, suggesting that POP2 transcription may be sensitive to glucocorticoids. Since glucocorticoids are used for treatment of inflammatory conditions, an impact on POP2 might be reflected by an increase in POP2-sensitive inflammatory processes during glucocorticoid use. Indeed, the role of NF-kB and inflammatory cytokines in acquired glucocorticoid resistance is appreciated, but incompletely understood. While additional studies may help determine the role of the DNA sequence sites mediating transcription of POP2, the minimal promoter elements necessary to induce NF-κB mediated POP2 transcription are present in the present invention.

As described below, POP2 mRNA is increased as early as 10 min following LPS or TNF-α stimulation of THP-1 or primary macrophages suggesting rapid stabilization of otherwise unstable POP2 message. Indeed, an initial examination of mRNA decay and half-life confirms that POP2 mRNA has a short half-life, similar to that of TNFα, as more than 50% of its message was degraded by 30 min post-LPS stimulation in THP-1 cells. Mechanistically, a 3' ARE element plays a role in this degradation. However, while the Wt ARE sequence is highly destabilizing, mutation of this element only partially restores POP2 expression, suggesting another stability regulating mechanism beyond the ARE. Rapidly induced NF-κB-dependent genes frequently contain multiple AREs in their 3'UTR mediating their rapid turnover. However, only one other potential ARE with a near-consensus sequence exists in the POP2 3'UTR (5'-ATTTTG-3') which may or may not serve to destabilize POP2 message. A non-consensus A-U rich region in POP2 could also modulate stability of the mRNA as A-U rich message destabilizing sequences lacking a consensus ARE have been described. Further, RNA binding proteins with either stabilizing or destabilizing function possessing varied affinities for particular ARE sequences may participate. Nevertheless, the entire POP2 3'UTR (SEQ ID. NO. 3) through the poly-A signal (SEQ ID NO: 4), and thus whatever other regulatory sequences contributing to POP2 stability/decay, was used in the POP2 transgene construct of the present invention as it is likely contribute to regulated expression in POP2 transgenic mice. The minimal promoter region necessary for POP2 expression was located and used, including sites needed for NF-κB-mediated transcription, and a likely important ARE-mediated function of its 3'UTR was identified.

Prior to generating transgenic mice, J744 mouse macrophages were first reconstituted with the POP2 transgene (SEQ ID. NO: 5) to validate expression and function of POP2 in cells originating from a mouse. Transfectants constitutively expressing POP2 produce less TNFα and IL-1β upon exposure to TLR ligands and following bacterial infection. Further, we have yet to observe a difference in POP2 function between mouse and human macrophages in our structure/function analysis. Likewise, stable POP2 transgene transfectants of J774 cells, although exhibiting minimal to absent expression of POP2 without stimulation, exhibit markedly reduced production of various NF-kB-dependent cytokines and reduced processing of IL-1β. Having confirmed induction of POP2 gene expression and function in a mouse macrophage cell line, transgenic mice were generated using the POP2 transgene to begin elucidating the physiologic role of POP2 in various inflammatory conditions.

POP2 mice are physically indistinguishable from LMC mice. Gross and microscopic anatomic analyses of tissues revealed no difference in structural organization or size of any organs between POP2 and LMC mice suggesting that the POP2 transgene has no obvious impact upon developmental processes. Largely consistent with the expression of POP2 in human testis and at low levels in hematopoietic cells, POP2 mRNA was expressed constitutively in the spleen, lymph nodes, and testis of POP2Tg mice with little to no message detected in other tissues. The lack of splenic expression in human samples is intriguing, but may simply reflect a rapid loss of POP2 message due to time constraints during isolation of this organ. Immunophenotyping of immune cells from various compartments by multi-color flow cytometric analysis revealed no obvious differences between basic populations of thymocytes, single positive T cells, B cells, NK cells, macrophage and neutrophils from POP2 and LMC mice, with the exception of increased numbers of splenic neutrophils. This increase could result from extramedullary myelopoiesis in the spleens of POP2 mice. Although it remains possible that POP2 might prevent splenic neutrophil death or in some way favor neutrophil development, it is unclear why such an effect would not be evident in blood or lymph nodes. Curiously, an increase in neutrophils was also noted in the peritoneum, but this difference was not statistically significant. Nevertheless, myeloid cells, T cells, and B cells all constitutively express POP2 which accounts for its expression in secondary lymphoid tissues. The lack of obvious developmental impacts, especially in the hematopoietic compartment is interesting and largely suggests that expression of POP2, at least at the mRNA level, is not detrimental in any way.

POP2Tg mice are relatively resistant to LPS-induced septic shock or bacteria-induced septicemic death, possibly due to reduced production of proinflammatory cytokines. Consistently, POP2Tg mice had reduced serum levels of IL-1β, IL-6, IL-12, IL-18, TNFα and MCP-1; all of them are NF-kB dependent transcriptional targets, demonstrating that POP2 elicits an inhibitory or negative regulatory effect on NF-κB pathway during inflammatory process. Additionally, POP2 mice were protected against acute bacterial infections with a delay in mean time to death and greater survival than LMC mice following *F. novicida* or *F. tularensis* LVS infection. This suggests that POP2 has regulatory effect on inflammatory process, specifically during the early period of acute infection. Although the kinetics of this regulatory effect is unknown, but it might be overcome or sustained at later time in the course of infection. Further, in humans, the impact of POP2 on inflammatory process could be coordinated with other POP proteins, including POP1, POP3, and POP4, as well as CARD-only proteins (COP1, INCA, and ICEBERG). As most of these genes are also absent in mouse and most non-primate species, additional single and multiple transgenic mouse models will be needed. Nevertheless, delaying the onset of inflammatory processes and excessive inflammation may be beneficial in providing a window of opportunity for the host to mount adaptive responses while avoiding or limiting damage to the host tissues.

The resistance of POP2Tg mice to LPS injection supports the observed capacity of POP2 to limit activation of human NLRP3 and mouse Nlrp3 inflammasomes and is consistent with the resistant phenotype of Nlrp3−/− mice against LPS shock. Moreover, in vitro activation of the Nlrp3 inflammasome was blunted in POP2Tg mouse macrophages obtained from bone marrow, spleen, or peritoneum. The results demonstrate that POP2 inhibits both the human AIM2 and mouse Aim2 inflammasomes as seen by the diminished response of POP2Tg macrophages to the dsDNA analog and Aim2 ligand poly(dA:dT). Interestingly, POP1 has not been described to limit the activation of any inflammasome and POP4 lacks key residues required for NLRP3 inflammasome inhibition, but POP3 inhibits the AIM2 inflammasome. With the addition of AIM2 as a verified target of POP2, it appears that POP2 acts more broadly than the other POPs.

Quantitatively, there was a significant reduction in ASC-containing specks in POP2Tg cells suggesting that POP2 reduce ASC speck formation. Interestingly, multiple ASC-specks per cell were observed in wild-type cells, which was unusual as most often ASC-specks appear as a large, single, perinuclear aggregate. Indeed, in HeLa cells, ASC association is very rapid upon cellular stimulation and that it is an energy favorable reaction, makes it very unlikely that more than one speck would form in a cell. Potentially, the multiple specks were aggregates that were "moving" towards each other and would formed one large peri-nuclear speck had more time elapsed. This possibility seems unlikely though, as these were overnight infections, thus allowing plenty of time for complete, single speck formation that has been observed in THP-1 cells infected similarly. However, there exists a splice variant of ASC, detected in THP-1 cells among others, which lacks the proline and glycine-rich (PGR) domain between the PYD and CARD domain, but can still process IL-1β. It has been demonstrated that this splice variant of ASC, produces branched and diffuse ASC specks. Thus, potentially, a certain level of POP2 expression prevents splicing of the smaller ASC that could be inducing the multiple pecks observed in wild-type cells.

The presence of POP2Tg prevents cell death in macrophages infected with Fn or Ft LVS, as it inhibits Asc/Aim2- and Asc/Nlrp3-inflammsome formation. This suggests that POP2 might prevent both caspase-dependent and independent cell death in macrophages, which could serve as a pro-survival factor in mice. Supporting this, massive necrosis and macrophage cell death in lungs has been implicated in acute death of Ft LVS-infected mice. Contrastingly, a dichotomous pattern has been reported in relation to macrophage cell death and survival of mice between Wt and Asc KO or Casp-1 KO mice. A similar dichotomy exists for susceptibility/resistance patterns to Anthrax lethal toxin versus spores. However, the results with POP2 mice indicate that the overall nature of the inflammatory response is more important for clinical outcome of the disease than the immediate fate of macrophages, although this remains to be investigated.

The findings collectively demonstrate that human POP2 under the control of its endogenous regulatory elements exhibits expression patterns and functions in mice that are expected and consistent with our current understanding of POP2 from studies with human tissues and cells. NF-κB dependent cytokine production is restricted, the activation of both NLRP3 and AIM2-dependent inflammasome assembly is diminished with tempered IL-1β release, and inflammasome associated macrophage cell death is reduced. That POP2Tg mice exhibit greater resistance to LPS-induced shock and certain bacterial infections supports our hypothesis that humans possess POPs, and related COP proteins, to provide higher-order regulation of inflammation to limit inflammation-associated damage. In this circumstance, the role of POP2 is highly appreciated as the results of this study underscore a fundamental and inherent difference between higher-order primates and rodents in susceptibility to certain microbial pathogens. For example, Fn and Ft LVS are highly pathogenic to mice, but non-pathogenic to humans. However, when POP2 gene was introduced into the mouse, the transgenic mice ('humanized') show a resistance to infection by Fn and Ft LVS suggesting that POP2 gene play a vital role in primates by modulating host immune responses and thereby susceptibility to microbial infections. However, the effect of POP2 in modulating immune responses in other microbial infections needs to be studied.

EXAMPLE

Characterization of Genetic Regulatory Elements Controlling Human POP2 Expression Human POP2 is a small (97 aa) protein encoded by a primate-restricted single exon gene on chromosome 3. Because POP2 inhibits NF-kB and NLRP3 inflammasome activity and reduces TNFα and IL-1β production by macrophages, functionally POP2 is thought to regulate inflammatory processes in vivo. Although POP2 expression is increased several fold in THP-1 cells and primary human monocytes treated with LPS, PMA or TNFα, the genetic element that controls POP2 expression is unknown. As these stimuli mimick the inflammatory environment and strongly induce NF-κB activation, it is presumed that POP2 expression might be regulated by NF-κB. To test this theory, the POP2 genomic locus upstream of the ATG start codon was analyzed and, as a result, two NF-κB consensus binding sequences and a putative TATA box element was identified at −24, −36, and −82 nt upstream of the POP2 ATG start codon, respectively, as seen in FIG. 1. Two putative initiator (Inr) elements were also observed at −70 and −46 nt, although a definitive transcriptional start site (TSS) has not yet been identified. To better establish the requisite upstream promoter region driving endogenous, inducible expression of POP2, 2000 bp of genomic sequence immediately upstream of the POP2 coding region was cloned in a luciferase reporter vector (POP2-Luc(-2000)). In transfected HEK293T cells, POP2-Luc(-2000) drove minimal production of luciferase comparable to that of the pGL3-basic vector only control, as seen in FIG. 1(*a*). In contrast, co-transfection of the NF-κB p65/RelA subunit resulted in 2 to 3-fold increase in POP2-Luc (-2000) luciferase activity, as seen in FIG. 2(*a*) and (*b*), strongly suggesting that expression of POP2 from its endogenous promoter is NF-κB responsive.

To identify the NF-κB responsive region, 5' truncations were made in the POP2-Luc (-2000) construct including (-505), (-250) and (-127). Interestingly, luciferase activity from all the constructs was comparable in presence of p65, as seen in FIG. 2(*b*), suggesting that the NF-κB responsive element is further downstream of −127 and is consistent with the location of the two downstream NF-κB consensus sites described above. The POP2 promoter region also contains a putative TATA box element at −82 bp, a feature consistent with TFIID-driven promoters and potentially indicative of a nearby, downstream TSS. To test the potential requirement for a TATA box, the TATA sequence was mutated in POP2-Luc (-127) and an approximately 2 or 3-fold reduction in p65-driven luciferase activity was observed in comparison to the wildtype POP2-Luc (-127) reporter, as seen in FIG. 2(*c*). These data reveal that POP2 contains a necessary TATA box and that sequences within the first 127 nt upstream of the coding sequence are sufficient for NF-κB induction of POP2. Further, BLAST searches of the mouse and the new world primate Otolemur garnetti genomes were performed with the 2000 bp sequence. These two species represent a range of species lacking POP2 as the ancestral locus was formed by a likely retrotransposition event near the divergence of old and new world primates. This comparison revealed syntenic mouse and Otolemur sequence at nt −319 through −1127 (65% identity) and nt −297 through −594 (71% identity), respectively, with no syntenic hits for sequence further downstream (data not shown). These corresponding syntenic sequences almost certainly predate the insertion of the NLRP2/7-like retrogene, suggesting that non-conserved DNA downstream of −319 nt most likely contain the sequences responsible for constitutive and inducible POP2 gene expression. Although not fully characterized, the necessary promoter region of POP2 appears likely to be quite small, a feature consistent with other evolutionarily recent genes.

Preliminary evaluation of POP2 expression in THP-1 and primary monocytes revealed the rapid induction (within 10 minutes) of POP2 mRNA by LPS and suggest likely posttrancriptional regulation of mRNA stability. To confirm this hypothesis, THP1 or U937 cells were treated with cyclohexamide (CHX) to prevent translation of proteins responsible for mRNA degradation. In these cells, POP2 mRNA expression was increased by 5 min following CHX treatment and did not decrease throughout the assay, as seen in FIGS. 2(d) and (e), supporting the conclusion that protein synthesis is required to maintain resting levels of POP2 mRNA. This observation also suggests that POP2 is continuously transcribed and that mRNA turnover is rapid. The decay of POP2 mRNA in THP-1 cells treated with the RNA polymerase II inhibitor Actinomycin D (ActD) was examined following LPS stimulation. Within 30 to 60 minutes of ActD addition, POP2 mRNA expression declined to near baseline levels, as seen in FIG. 2(f). Pre-treatment of the cells with ActD completely blocked LPS-induction of POP2 mRNA, as seen in FIG. 2(g). These results indicate that turnover of POP2 mRNA is rapid with a roughly estimated half-life of 18 min in THP-1 cells. Finally, the rapid turnover and CHX stabilization of POP2 mRNA implicate stability-regulating elements within the POP2 transcript. Many inflammatory genes are regulated post-transcriptionally by A-U rich elements (AREs) in their 3' untranslated regions (3'UTR). Examination of POP2 3'UTR reveals a potential class III ARE (AUUUUA) similar to that of TNFα. As such, the presence of ARE in POP2 3'UTR in SV40-driven luciferase expression vector resulted in loss of approximately 90% of control activity, as seen in FIGS. 2(h) and (i). Further, mutation of the POP2 3' ARE sequence restores luciferase activity to slightly more than 50% of the control vector, confirming that POP2 message stability is partially controlled by a cis-acting ARE in its 3' UTR. In total, beyond identification of key regulatory sequences in the POP2 gene locus, these analyses demonstrate a need for attendant regulatory elements to maintain the expression of POP2 and to achieve its function in situ.

Genetic Reconstitution of Human POP2 in Murine Macrophages Recapitulates its Function Prior to generating a POP2 transgenic mouse, genetic reconstitution of mouse macrophages with a human POP2 transgene was performed to determine whether it would recapitulate its expression and function. From the newfound knowledge of the regulation of POP2 gene expression, a POP2 transgene (POP2Tg) containing 2000 bp of upstream sequence was generated (which encompasses the NF-κB responsive and likely complete promoter), the single exon coding sequence, and the stability regulating 3' UTR, as seen in FIG. 3(a). An HA-tag sequence (SEQ ID NO: 6) was added to ensure a detectable protein epitope. This construct prevented constitutive expression of POP2 and conferred LPS inducibility in transfected RAW264.7 cells, as seen in FIG. 3(b). As the function of constitutively expressed POP2 in the mouse macrophage cell line J774A.1 has been characterized, stable POP2Tg transfectants were produced in these cells. In two independent transgenic clones (Tg 1 and Tg 4), LPS induced expression of POP2 mRNA and POP2 protein, as seen in FIGS. 3(c) and (d), confirming further that the regulatory elements of the POP2Tg confer inducibility similar to that observed with human cells.

To assess the regulatory function of POP2 in J774A.1 macrophages, POP2Tg clones were treated with LPS or infected with *Francisella novicida* (Fn). It was found that these cells produced less IL-1β and TNFα, as seen in FIG. 3(e), consistent with the inhibition of NF-kB pathway by POP2. Also, POP2Tg effectively blocked IL-1β production in LPS-primed transfectant clones treated with ATP or nigericin for 40 min, as seen in FIG. 3(f), consistent with inhibition of Nlrp3 inflammasome. In mouse macrophages, Fn infection is thought to activate the Aim2 inflammasome without activating Nlrp3. Since Fn infection of our POP2Tg J774A.1 cells yielded less IL-1β, as seen in FIG. 3(e), and because Aim2 contains an N-terminal PYD domain, it was reasoned that POP2 might also disrupt the function of Aim2 inflammasome. Indeed, POP2Tg inhibited IL-1β production in LPS-primed J774A.1 transfectants treated with poly(dA:dT), an Aim2 agonist, confirming that POP2 inhibits Aim2 inflammasome, as seen in FIG. 3(g). To extend this observation and establish whether POP2 has a direct effect on this inflammasome, the human AIM2 inflammasome was reconstituted, with and without POP2, in HEK293T cells. In the absence of POP2, these cells constitutively process IL-1β, but when POP2 is present IL-1β production is markedly inhibited, as seen in FIG. 3(h). In addition, the oligomerization of ASC into 'specks' that hallmark the inflammasome assembly was monitored. Multiple small specks consistent with the pattern observed for Aim2 activation were observed in J774A.1 control transfectants infected with Fn, while fewer ASC specks were seen in POP2Tg cells, as seen in FIGS. 1(a) and (b). Infection with Fn also triggers caspase-1-dependent, pyroptotic cell death via Aim2. POP2Tg cells showed a reduced cell death when compared to pcDNA3 cells after Fn infection, as seen in FIG. 1(c), suggesting that POP2 prevents Aim2/caspase-1-dependent pyroptosis in these cells. Interestingly, POP2 reduces the level of IL-1β in J774A.1 trasnfectants infected with *Listeria monocytogenes* (which activate Nlrp3 inflammasome), but not in those transfectants infected with *Salmonella typhimurium* (the intracellaulr bacterium engage Nlrc4 inflammsomes), as seen in FIG. 3(i), suggesting that POP2 has no role on Nlrc4 inflammasome. Collectively, these data demonstrate that POP2 reduces AIM2 and Nlrp3 inflammasomes activity in both mouse and human cells.

Generation of Human POP2 Transgenic Mice

To study the regulatory role of POP2 in vivo, specifically on NF-kB and inflammasome pathways, POP2Tg mice expressing human POP2 were generated using the transgene construct described above. Two founders of POP2Tg mice (a male and a female) were generated on the C57BL/6×Balb/c background and the male founder successfully transmitted the POP2 transgene in the initial backcross to C57BL/6. Both POP2Tg and littermate control (LMC) pubs showed no birth defects or difference in general phenotypes and pre- and post-weaning behaviors. Both male and female POP2Tg mice are fertile and there are no apparent differences in age of sexual maturity. Litter size, body weight, weight of major organs, and sex distribution within litters and among POP2Tg and LMC mice were also unaffected, as seen in FIG. 4(a) through (g). The POP2 transgene is successfully transmitted and displays no sex bias, as seen in FIG. 5(a) and FIG. 4(b). Feeding, watering, urination, defecation, and respiration of POP2Tg mice are also indistinguishable from those of LMC as were gait, alertness, and grouping behaviors. These results were obtained from POPTg mice backcrossed to C57BL/6 for six generations (N6) and beyond. On gross examination, vital organs (kidneys, spleen, heart, lungs, testes, bladder, liver etc.) and lymphoid organs (spleen, thymus, lymph nodes etc.) were found to be normal in size and structure without any defects in POP2Tg and LMC mice, as seen in FIG. 6. Also, histological analysis of individual organs revealed no appreciable changes in tissue architecture between POP2Tg and LMC mice, as seen in FIG. 7.

To compare the expression pattern of POP2 in mouse tissues to previously published human data, mRNA analysis was performed for POP2 using perfused organs from POP2Tg and LMC mice. Initial RT-PCR analysis revealed POP2 expression in mouse testes, thymus, spleen, peripheral lymph nodes (pLN), heart, liver, kidney and lung, as seen in FIG. 5(b). Quantitation of POP2 mRNA revealed highest expression in the spleen, testes, and lymph nodes, with much lower expression in the thymus, as seen in FIG. 5(c). POP2 expression was also detected in the bone marrow cells and peripheral blood mononuclear cells, as seen in FIG. 5(d). In the bone marrow, CD11b-cells account for most of the constitutive POP2 mRNA expression, as seen in FIG. 5(e), while T, B, and dendritic cells (DC) isolated from spleen express POP2 to varying degrees, as seen in FIG. 5(f). No difference in expression was observed between sexes for spleen, pLN or thymus. As expected, no POP2 was detected in any organs or isolated cells from LMC mice (data not shown). Consistent with the PCR analysis, POP2 protein was detected in macrophages, DC, T and B cells isolated from both spleen and bone marrow, as seen in FIG. 5(g). POP2 protein was similarly detectable in tissue sections of spleen of POP2Tg mice, but not those of LMC, as seen in FIG. 5(h). Curiously, despite its expression in isolated human hematopoietic cells, POP2 was not detected previously in cDNA from human spleen. This discrepancy may reflect a loss of POP2 mRNA in human spleen samples due to a short mRNA half-life and/or differences in organ processing, such as live versus cadaveric donors, and the time to sample preparation. Nevertheless, the pattern of POP2 expression observed in POP2Tg mice is generally highly consistent with that observed using human cDNA panels, recapitulating expression in testes, peripheral blood cells, including various myeloid and lymphoid populations.

Immunophenotyping of POP2 Mice

Since NF-κB is important for cell growth, development, and differentiation as well as controlling expression of various cytokine genes, and because POP2 is a demonstrated negative regulator of NF-κB, such regulation could influence normal development of immune cells in POP2Tg mice. As such, immune cells in spleen, pLN, thymus, blood, peritoneal fluid and bone marrow were immunophenotyped. Within the lymphoid compartment, CD4+ or CD8+ T cells (CD3+ subset), B cells (CD3-subset) and NK1.1 cells were identified, as seen in FIG. 8(a) through (b) and the frequency and total numbers of lymphoid cells were comparable between POP2Tg and LMC mice, as seen in FIG. 8(c) through (f). The major myeloid-lineage cells were identified as neutrophils, macrophages and DC, as seen in FIG. 8(g) through (h). With the exception of an increased frequency of splenic Gr-1+ neutrophils and a slight decrease in splenic F4/80+ macrophages in POP2Tg mice, there was no change in other cell populations, as seen in FIG. 8(i) through (l). The frequency and total numbers of both CD4+CD25+FoxP3+ Tregs and CD4+IL-17+ T cells were also comparable between POP2 and LMC mice in spleen and pLN (data not shown).

POP2 Moderates the Cytokine Production in Macrophages by Inhibiting Nlrp3 and Aim2 Inflammasomes and NF-kB Pathway In human monocytes/macrophages, POP2 inhibits NF-kB and inflammasomes. To confirm whether POP2 moderates the level of pro-inflammatory cytokines in transgenic mice, we harvested macrophages from bone marrow (BMDM), peritoneum or spleens of POP2Tg and LMC mice and treated with LPS plus Nlrp3 (ATP and nigericin) or Aim2 (poly(dA:dT) inflammasome activtors. POP2Tg BMDM produced significantly ($p<0.05$) less IL-1β IL-18, IL-6 and TNFα than that of LMC mice, as seen in FIG. 9(a)-(d). Like BMDM, LPS-primed peritoneal macrophages of POP2 mice produced significantly ($p<0.05$) less IL-1β, IL-18, TNFα and IL-6 when compared to macrophages of LMC mice, as seen in FIG. 9(e) through (h). Interestingly, splenic macrophages of POP2 mice also produced significantly ($p<0.05$) less IL-1β, IL-18 and TNFα (FIG. 6i-k), but comparable level of IL-6 to that of LMC mice, as seen in FIG. 9(l). These results confirm the unique function of POP2 to inhibit NF-kB signaling and both Nlrp3 and Aim2 inflammaosmes in macrophages.

POP2 Mice Exhibit Resistance to LPS-Induced Endotoxemic Shock

Since POP2 inhibits NF-κB and inflammasomes in vitro, it was hypothesized that the normal physiologic role of POP2 is to limit excessive or uncontrolled inflammatory responses in vivo. To explore such a role, lethal septic shock was induced in POP2Tg and LMC mice by intraperitoneal injection of lethal dose of LPS (50 mg/kg). LMC mice were found to be 100% susceptible to lethal dose of LPS at 48 hours post-injection, while POP2Tg mice displayed a significant ($p<0.05$) delay in time to death with 20% of the mice surviving, as seen in FIG. 10(a). LPS toxicity in wild-type mice is accompanied by increased proinflammatory cytokine production, while numerous knockout mice exhibit resistance to LPS as a consequence of decreased NF-κB activation with concomitant decreases in proinflammatory cytokines including TNFα, IL-1β, and others. In contrast, the levels of TNFα, IL-6, and CXC cytokines are less abundant in septic patients and do not reach peak levels until later in the response. Because POP2 can diminish NF-κB-mediated cytokines, the resistance to LPS by POP2Tg mice could be attributed to an altered inflammatory cytokine profile. As such, basal cytokines levels did not differ between naive POP2Tg and LMC mice, but there was a significant ($p<0.05$) reduction in serum levels of IL-1β, IL-18, IL-6, IL-12, TNFα and MCP-1 in POP2Tg than LMC mice at 24 h following sub-lethal dose (15 mg/kg) of LPS, as seen in FIG. 11(b) through (h). However, serum IL-10 levels were not significantly different between POP2 and LMC mice, as seen in FIG. 10(i). These results demonstrate that POP2 reduces the level of pro-inflammatory cytokines by inhibiting NF-κB- and inflammasome pathways. Consistently, the moderation in level of these cytokines favors survival of POP2Tg mice but not LMC mice during LPS-induced endotoxemic shock.

POP2Tg Mice are Less Susceptible to Acute Bacterial Infections

POP2 inhibits NF-kB and inflammasomes in macrophages and POP2 mice are resistant to LPS-induced endotoxemia through reduced serum TNFα, IL-6, IL-1β and IL-18 levels, consistent with previous studies demonstrating that elevated pro-inflammatory cytokines in response to TLR-mediated NF-kB signaling leads to endotoximic death. As such, it was hypothesized that inhibition of NF-kB or inflammasomes by POP2 might be detrimental during in vivo bacterial infections. To test this, the gram-negative bacterium Fn was used. Fn activates a NF-kB-mediated cytokine storm resulting in septicemic death of mice. Mice are highly susceptible to Fn, which primarily activates Aim2 inflammasome and survival requires an Aim2, ASC, and Caspase-1-dependent inflammasome response and IL-1β production. POP2 and LMC mice were subcutaneously infected with Fn ($1.5 \times 10^5$ cfu) as described previously. Clinical signs of infection appeared early in LMC mice with 50% dying before day 5 and 70% by day 8 post-infection, as seen in FIG. 11(a). Curiously, POP2 mice did not reach 50% mortality until day 8 and no further mortality was observed.

However, changes in body weight were comparable between both groups of mice, as seen in FIG. 12(a). Although anticipated to diminish survival of Fn infected POP2 mice, these mice are less susceptible to Fn infection, as evidenced by a three day delay in mean time to death and greater overall survival. This result could be due to the effect of reduced levels of pro-inflammatory cytokines (e.g., TNF and IL-1β), as seen in LPS toxicity study described above. However, recent studies have shown that IL-1β is protective during various microbial infections including pulmonary infection and specifically inflammatory monocytes recruited to the lung help in clearing infection, where POP2 might again be detrimental. Therefore, we also considered the impact of POP2 in the context of intranasal infection with Ft LVS which causes an acute necrotizing pneumonia and activates Nlrp3 inflammasome. Since mice deficient in TLR2 are highly susceptible to Ft LVS infection, it was anticipated that there would be a higher susceptibility of POP2Tg mice by reducing TLR2-dependent NF-kB activation and/or through reducing inflammasome-dependent IL-1β. Surprisingly, POP2Tg mice were significantly protected against a sub-lethal infectious dose (750 cfu; ~LD70) of F. tularensis LVS with delayed mortality compared to LMC mice, as seen in FIG. 12(b). Surviving POP2 mice also recovered body weight more rapidly than surviving LMC mice, as seen in FIG. 12(b). Collectively, these results demonstrate that POP2, while capable of reducing systemic inflammation, is unlikely to be detrimental during bacterial infection and instead plays a protective role.

To confirm the protection against Ft LVS in POP2Tg mice, the bacterial burden in lungs was examined, as seen in FIG. 12(c). While infection is established in POP2Tg mice and the bacteria replicate over the initial 3 days to levels similar to those in LMC, by day 6 the bacterial burden is decreased by approximately a magnitude of one log. Because improved resistance was counter-intuitive to the role of TLR-dependent cytokines, it was considered whether inflammatory cytokines levels might be maintained or improved in the lung of Ft LVS infected mice. On 1 and 3 dpi, no appreciable differences in these cytokines were noted between POP2Tg and LMC mice, as seen in FIG. 12(c) through (d). On 6 dpi, however, the production of IL-1β, IL-18, IL-6, and TNFα were all significantly diminished in POP2 mice, demonstrating that reduced levels of these cytokines in the lung does not increase mortality and instead favors survival. This suggests that unrestrained inflammation mediated by elevated cytokines is responsible for lethal F. tularensis infection. Curiously, IFNγ was increased in the lungs of POP2 mice, suggesting that reduced bacterial burden may result from IFNγ-enhanced macrophage bacteriostatic activity in the lungs of these mice and could also signal improved Th1/Th17 responses associated with improved resistance to F. tularensis.

That Ft LVS infected POP2Tg mice were better protected than those infected with F. novicida lead to consideration whether the response of POP2Tg macrophages to these two bacterial strains might differ. While F. novicida infection of BMDM elicits a stronger IL-1β and IL-18 responses and a lower TNFα response than that seen with Ft LVS, the presence of POP2 similarly reduces both cytokines irrespective of the bacterial strain. However, the level of IL-6 was not different between POP2 and LMC mice. Thus, although it is possible that higher IL-1β production by infected macrophages in vivo might account for the relative inability of POP2 to protect mice against F. novicida infection, it is more plausible that other differences very likely contribute. For instance, survival of mice infected with F. novicida correlates positively with pyroptotic macrophage cell death mediated by the Aim2-Asc-Caspase-1 axis. Thus, macrophage death following infection with Ft LVS and F. novicida was compared. As expected, macrophages from POP2 mice exhibited less cell death than control macrophages at 24 hours post-infection. Although macrophage survival was expected to presage greater host susceptibility to infection, the opposite was observed. While POP2Tg macrophages are less susceptible to infection-mediated death, POP2Tg mice survive at least as well, if not better, than controls. The presence of POP2 thus seems to abrogate the correlation between the in vitro macrophage response and the in vivo response of the mouse, suggesting that in POP2 mice the nature of the macrophage response likely differs during in vivo infection.

Collectively, these observations demonstrate that while limiting the detrimental inflammatory responses contributing to septic shock, POP2 does not generally decrease resistance to bacterial infection. These features are consistent with the expected role of a bona fide inflammatory regulator and establish the hypothesis that POP2 beneficially regulates otherwise harmful inflammation. Further, POP2-mediated control of inflammatory responses during infection may favor protective responses by redirecting the cytokine and anti-bacterial activities of recruited inflammatory macrophages.

POP2Tg mice according to the present invention could be used for studies of the role of POP2 in human health and disease, for testing drugs or other therapies targeting at reducing inflammation through modulating POP2 expression and/or function, for testing drugs or other therapies targeting at modulating inflammation, influencing disease states, or preventing harmful side-effects where POP2 expression and/or function contributes to the biological process. As these mice are humanized (i.e. they express a protein that humans possess, but mice lack), they represent a potential resource for studies related to human inflammation without requiring human subjects, thus allowing a wider range of approaches.

What is claimed is:

1. A transgenic mouse whose genome comprises a human pyrin-domain only protein 2 (POP2) transgene comprising 2000 base pairs upstream of a human POP2 gene coding region, a single POP2 exon coding sequence, and a 3' untranslated region sequence, wherein the mouse expresses the POP2 transgene and has a phenotype of reduced production of proinflammatory cytokines in response to LPS-induced shock and bacterial infections when compared to a control mouse.

2. The transgenic mouse of claim 1, wherein the tissue expression pattern of the POP2 gene in the mouse is consistent with the tissue expression pattern of the POP2 gene in a human.

3. The transgenic mouse of claim 2, wherein the transgene comprises SEQ ID NO: 1.

4. The transgenic mouse of claim 3, wherein the genome of the mouse is on a C57BL/6 background.

5. A method of producing a transgenic mouse, comprising the steps of:

microinjecting a human pyrin-domain only protein 2 (POP2) transgene comprising 2000 base pairs upstream of a human POP2 gene coding region, a single POP2 exon coding sequence, and a 3' untranslated region sequence into a fertilized mouse oocyte;

transferring said fertilized oocyte to a pseudopregnant female mouse;

allowing said transferred fertilized oocyte to develop to term; and identifying and selecting a transgenic mouse whose genome comprises the POP2 transgene and has a phenotype of reduced production of proinflammatory cytokines in response to LPS-induced shock and bacterial infections when compared to a control mouse.

6. The method of claim 5, wherein the tissue expression pattern of the POP2 gene in the mouse is consistent with the tissue expression pattern of the POP2 gene in a human.

7. The method of claim 6, wherein the transgene comprises SEQ ID NO: 1.

8. The method of claim 7, wherein the genome of the transgenic mouse is on a C57BL/6 background.

* * * * *

SEQUENCE LISTING

```
<160> NUMBER OF SEQ ID NOS: 6

<210> SEQ ID NO 1
<211> LENGTH: 318
<212> TYPE: DNA
<213> ORGANISM: Homo sapiens

<400> SEQUENCE: 1
atgtacccat acgatgttcc agattacgca tcttctgcag agctggactt caacctgcag        60
```

```
gctcttctgg agcagctcag ccaggatgag ttgagcaagt tcaagtctct gatcagaaca    120
atctccctgg gaaaggagct acagaccgtc ccccagacag aggtagacaa ggctaatggg    180
aagcaactgg tagaaatctt caccagccac tcctgcagct actgggcagg gatggcagcc    240
atccaggtct ttgaaaagat gaatcaaacg catctgtctg ggagagctga tgaacactgt    300
gtgatgcccc cacccttaa                                                 318

<210> SEQ ID NO 2
<211> LENGTH: 2000
<212> TYPE: DNA
<213> ORGANISM: Homo sapiens

<400> SEQUENCE: 2
gcatgccata ggaatttaac tcttgcttgt atgagttagc ctatgataaa attgtttttg     60
ttatacatca tttcattcaa agttgcagtt tccaagaatc tattgaggac attaagtgag    120
tattttgttc ttacaaataa tgctatgcaa gcagacacac ctgtaagaca atactagag     180 gtggaaaagc caggtcaaag agcaaatgct cttgtcgttt atattttca ggactgcctt     240 ctctagggtt catataaatt tatactcaat ctgaaacatg cactccaaaa aatacaagca    300
aattgaatac agtgacctat aaaaagaatt atacacaatg accaagtggg atttatcccg    360
ggacggcaag gttggtttga acatatgaaa atcaattaat ataattcatc atatcagtag    420
aataaaaaca aaaattacat gattatctca ataaacacag aaaaagcact ggacaaaacc    480
caacttcctt tcatgataaa aatactccca actggaaaat agaagggagc ttcctcaatc    540
tgataaaagt tatctatgaa aactcatagc caaaattata tttaatggaa aaatgatttt    600
tgtcctaaaa tcaggaccat ctcaatgcta tctgctctta gcatgaccat acaacattac    660
attagtggtg ctagccctag caactagaca agataagaaa ggcaactgga ttggaatgga    720
agtgaaagtg tctgtattag cagataacat aatcttgtat ataggaaatc ctaaaaaatt    780
cactcgaaac ctgttagaac tattaaatga gttcatccag gtttcaggat acaagatcat    840
acataaaaat cagttttttct tctacacact tgtaatgaac agtccaaaac tgaaattaaa    900
acaattcctt ttagaatcat atcaaaaaga ataaaatacc tagaaataaa ttttaacaaa    960
gaagtaaaac ttatgctctg aaaattacaa gacattattg agagaaatta aagagctaaa   1020
taagtggaaa gcatctcgtg tttatagatt ggaaggctta atttacattg ttaagatggc   1080
actactcccc aaactgatct acagattcaa tacaatccct gtcagaacct cagcttactt   1140
tatgtagaaa tgggcaaact agttagaaaa ttcaagtagt atcgcataga cccagtacag   1200
ccaagatgat attgaaaaat aagagcaaac aaagacaatt caccttttcct tatttcatga   1260 cttagtaatt tatttagtat ttcctcattt catgacttag catcttaatg gtaattaaga   1320
taatgtggta ctggcataag gataggcaca ttgctcaata aaacagaact gagagtccaa   1380
aaataagccc gtacatctgt ggtcaactga cttttcaacaa gggtttcaag accgtacaat   1440
ggggaaagaa tagactttttc aacaaatgat gcttaggcaa gtagatttct acatgcagaa   1500
gaataaagtt ggacctctat ttcatgccac atacaaaaat taactcaaaa tatatcaaat   1560
acccaaatgt aagagttaaa gctgtaatat tcttatagta aatgataggg gtacatcttt   1620
atgacctgag acttggcaaa agattcttag acatgacatc aaaagcataa aaaataagaa   1680
aaaaatagat aaatttgatt tcatcaaaat gaaaaacatt tgtaccttaa aggacaccat   1740
cattaaactg ataagacaac tcacagaatg ggagcaaaaa tttgcgtatc gcgtatctaa   1800
tgaaggacct gtccctagac tatataaaga actcttacaa ctcagcaata aaaagacaat   1860
```

-continued

| | |
|---|---|
| aacgcaattt tataatgagc aaaaatctga actgatattt cttctaaaaa gatataaaaa | 1920 |
| tatatactta ttagtatatg aaaaaatgtg agaaccagag catagggcca ggcgttggga | 1980 |
| gagctcccac ataggacaag | 2000 |

<210> SEQ ID NO 3
<211> LENGTH: 243
<212> TYPE: DNA
<213> ORGANISM: Homo sapiens

<400> SEQUENCE: 3

| | |
|---|---|
| cccctcaggg atagtgagtt gatggctgag ctagatgttg ctttagcctt ggttctgtct | 60 |
| ccatttaca tgcacatgtt gcttaacctt gttatatatg aaatatctat atcaccagta | 120 |
| ttttgagata aataaaggtg aaataattca caaacattaa aagaaaagat gcctgacaac | 180 |
| tttagtattc agggaaatgc aaatcaaaac tatgatgaga taccacttca tatccactag | 240 |
| gct | 243 |

<210> SEQ ID NO 4
<211> LENGTH: 7
<212> TYPE: DNA
<213> ORGANISM: Artificial Sequence
<220> FEATURE:
<223> OTHER INFORMATION: Polyadenylation signal sequence

<400> SEQUENCE: 4

| | |
|---|---|
| attaaaa | 7 |

<210> SEQ ID NO 5
<211> LENGTH: 2561
<212> TYPE: DNA
<213> ORGANISM: Artificial Sequence
<220> FEATURE:
<223> OTHER INFORMATION: POP2 transgene construct

<400> SEQUENCE: 5

| | |
|---|---|
| gcatgccata ggaatttaac tcttgcttgt atgagttagc ctatgataaa attgttttg | 60 |
| ttatacatca tttcattcaa agttgcagtt tccaagaatc tattgaggac attaagtgag | 120 |
| tattttgttc ttacaaataa tgctatgcaa gcagacacac ctgtaagaca aatactagag | 180 |
| gtggaaaagc caggtcaaag agcaaatgct cttgtcgttt atattttca ggactgcctt | 240 |
| ctctagggtt catataaatt tatactcaat ctgaaacatg cactccaaaa aatacaagca | 300 |
| aattgaatac agtgacctat aaaaagaatt atacacaatg accaagtggg atttatcccg | 360 |
| ggacggcaag gttggtttga acatatgaaa atcaattaat ataattcatc atatcagtag | 420 |
| aataaaaaca aaaattacat gattatctca ataaacacag aaaaagcact ggacaaaacc | 480 |
| caacttcctt tcatgataaa aatactccca actggaaaat agaagggagc ttcctcaatc | 540 |
| tgataaaagt tatctatgaa aactcatagc caaaattata tttaatggaa aaatgatttt | 600 |
| tgtcctaaaa tcaggaccat ctcaatgcta tctgctctta gcatgaccat acaacattac | 660 |
| attagtggtg ctagccctag caactagaca agataagaaa ggcaactgga ttggaatgga | 720 |
| agtgaaagtg tctgtattag cagataacat aatcttgtat ataggaaatc ctaaaaaatt | 780 |
| cactcgaaac ctgttagaac tattaaatga gttcatccag gtttcaggat acaagatcat | 840 |
| acataaaaat cagtttttct tctacacact tgtaatgaac agtccaaaac tgaaattaaa | 900 |
| acaattcctt ttagaatcat atcaaaaaga ataaatacc tagaaataaa ttttaacaaa | 960 |

```
gaagtaaaac ttatgctctg aaaattacaa gacattattg agagaaatta aagagctaaa   1020
taagtggaaa gcatctcgtg tttatagatt ggaaggctta atttacattg ttaagatggc   1080
actactcccc aaactgatct acagattcaa tacaatccct gtcagaacct cagcttactt   1140
tatgtagaaa tgggcaaact agttagaaaa ttcaagtagt atcgcataga cccagtacag   1200
ccaagatgat attgaaaaat aagagcaaac aaagacaatt cacctttcct tatttcatga   1260
cttagtaatt tatttagtat ttcctcattt catgacttag catcttaatg gtaattaaga   1320
taatgtggta ctggcataag gataggcaca ttgctcaata aaacagaact gagagtccaa   1380
aaataagccc gtacatctgt ggtcaactga ctttcaacaa gggtttcaag accgtacaat   1440
ggggaaagaa tagacttttc aacaaatgat gcttaggcaa gtagatttct acatgcagaa   1500
gaataaagtt ggacctctat ttcatgccac atacaaaaat taactcaaaa tatatcaaat   1560
acccaaatgt aagagttaaa gctgtaatat tcttatagta aatgataggg gtacatcttt   1620
atgacctgag acttggcaaa agattcttag acatgacatc aaaagcataa aaataagaa    1680 aaaaatagat aaatttgatt tcatcaaaat gaaaaacatt tgtaccttaa aggacaccat   1740
cattaaactg ataagacaac tcacagaatg ggagcaaaaa tttgcgtatc gcgtatctaa   1800
tgaaggacct gtccctagac tatataaaga actcttacaa ctcagcaata aaaagacaat   1860
aacgcaattt tataatgagc aaaaatctga actgatattt cttctaaaaa gatataaaaa   1920
tatatactta ttagtatatg aaaaaatgtg agaaccagag catagggcca ggcgttggga   1980
gagctcccac ataggacaag atgtacccat acgatgttcc agattacgca tcttctgcag   2040
agctggactt caacctgcag gctcttctgg agcagctcag ccaggatgag ttgagcaagt   2100
tcaagtctct gatcagaaca atctccctgg gaaaggagct acagaccgtc ccccagacag   2160
aggtagacaa ggctaatggg aagcaactgg tagaaatctt caccagccac tcctgcagct   2220
actgggcagg gatggcagcc atccaggtct ttgaaaagat gaatcaaacg catctgtctg   2280
ggagagctga tgaacactgt gtgatgcccc caccttaacc cctcagggat agtgagttga   2340
tggctgagct agatgttgct ttagccttgg ttctgtctcc attttacatg cacatgttgc   2400
ttaaccttgt tatatatgaa atatctatat caccagtatt ttgagataaa taaaggtgaa   2460
ataattcaca aacattaaaa gaaaagatgc ctgacaactt tagtattcag ggaaatgcaa   2520
atcaaaacta tgatgagata ccacttcata tccactaggc t                      2561

<210> SEQ ID NO 6
<211> LENGTH: 24
<212> TYPE: DNA
<213> ORGANISM: Artificial Sequence
<220> FEATURE:
<223> OTHER INFORMATION: HA epitope tag

<400> SEQUENCE: 6
tacccatacg atgttccaga ttac                                            24
```